United States Patent

Halstead

Patent Number: 5,309,279
Date of Patent: May 3, 1994

[54] SCRIPT VIEW A CURVED CONVEX MAGNIFYING DEVICE

[76] Inventor: Madeline C. Halstead, Rte. 2 Box 669 Bain La., Mooresville, N.C. 28115

[21] Appl. No.: 934,353

[22] Filed: Aug. 21, 1992

[51] Int. Cl.⁵ .............................................. G02B 27/02
[52] U.S. Cl. ................................. 359/442; 359/802; 359/811
[58] Field of Search ............... 359/802, 803, 809, 810, 359/811, 804–805, 436, 440–442; D16/135

[56] References Cited

U.S. PATENT DOCUMENTS

| | | | |
|---|---|---|---|
| D. 194,995 | 4/1963 | Hoogesteger et al. | D16/135 |
| D. 243,329 | 2/1977 | Snarski | D16/135 |
| D. 296,792 | 7/1988 | Lewis | D16/135 |
| 307,775 | 11/1884 | Kirk et al. | 359/810 |
| 1,367,879 | 2/1921 | Laird | 359/809 |
| 2,389,282 | 11/1945 | Stegeman | 359/811 |
| 2,787,937 | 4/1957 | Prisament | 359/809 |
| 2,961,108 | 11/1960 | Johnson | 359/809 |
| 3,052,158 | 9/1962 | Sonni | 359/809 |
| 4,137,863 | 2/1979 | Anglin | 359/811 |
| 5,204,775 | 4/1993 | McDevitt | 359/811 |

*Primary Examiner*—Loha Ben
*Assistant Examiner*—James Phan

[57] ABSTRACT

An optical instrument for magnifying printed or written material on three dimensional round or oval containers or objects. The instrument is an arced convex lens which provides distortion free magnification of multiple lines of text inscribed around the circumference or perimeter of vials, bottles, or other curved objects, while staying self affixed. The instrument is simply slid up or down, if required, to magnify the chosen text.

2 Claims, 1 Drawing Sheet

SCRIPT VIEW A CURVED CONVEX MAGNIFYING DEVICE

FIELD OF INVENTION

This invention relates to magnification devices more particularly to self affixed magnifiers which match the contour of the object needing magnification.

BACKGROUND—PRIOR ART

Millions of people take prescriptions and over-the-counter medications every day to improve or maintain their health. Tragically medication errors occur when the wrong medication, the wrong dosage, or an incompatible combination of medications is taken. The print on prescription labels and medication bottles frequently is small and difficult to read.

In 1960, F. S. Johnson, U.S. Pat. No. 2,961,108 addressed the problem when he invented a magnifying cap for medicine bottles. However, this required action and effort by the user to hold it over the print since it was not self affixed, nor did it match the contour of the bottle. Distortion results due to the motion involved and inconsistent distance between container and magnifier. Hand held magnifiers are also unsuitable for the same reasons.

Previous inventors: Kirk, Brayton, Wader and Oulehen Ser. No. 307,775, 1884; W. G. Laird U.S. Pat. Nos. 1,367,879, 1921; R. Stegeman 2,389,282, 1945; J. Prisament 2,787,937, 1957; and A. Sonni 3,052,158, 1962; created affixed magnifiers for burettes, thermometers, insulin syringes and like but none of these magnifiers go beyond the planar two dimensional realm. None of them match the contour of the item in need of enlargement nor are they suitable for magnification of text written around the circumference or perimeter of containers or other curved objects.

Prior art is limited to magnification of flat material. In none of the prior art reviewed is there a magnifier which goes beyond the linear scope and is suitable for use with inscription which wraps around curved objects.

Applicant wishes to make of record the following U.S. patents as the closest known prior art which utilize plano convex lenses Hoogesteger, Brighton, and Pitchford Des. Ser. No. 194,995, 1963; and Anglin U.S. Pat. No. 4,137,863, 1979.

OBJECTIVES AND ADVANTAGES

The first and foremost object of this curved convex magnifying device is to promote safety by enlarging the inscription on labels especially those on prescription vials so that the likelihood of misreading important information, and subsequent medication errors can be reduced.

Another object is to provide optically clear magnification of multiple lines of text inscribed around the circumference or perimeter of a container by means of a device that is self affixed.

There are several advantages of the above mentioned device. This device's smooth and protuberant shape is easier for stiff hands to manipulate. It is simple to construct, economical to manufacture, durable, and simple to use. It can be reused on other objects of the same shape and size, and can be fabricated of recyclable synthetic resins. Additionally, this magnifying instrument provides convenience by being tension self-affixed, thereby the magnifying device stays in place ready for use.

These and other objects and advantages will become clear after a reading of the following description and drawings.

DESCRIPTION OF THE INVENTION

Figure 1:
FIG. 1 is a perspective view of one form of the curved convex lens shown in place over a prescription vial.
Figure 2:
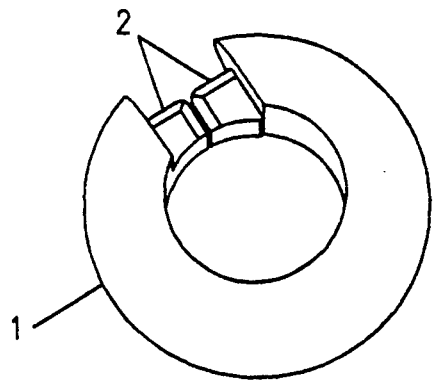
FIG. 2 is an top isometric view of the instrument. A bottom isometric view would be identical.

The magnifying instrument shown in FIGS. 1-6, is primarily designed to be slid onto prescription medication vials and over-the-counter medication bottles, although it is not limited to such. Referring to FIG. 2, the magnifier is shown to be composed from one solid piece of transparent material fabricated to include the arced convex lens body 1, and tapered end tabs 2. The instrument is constructed of an optically clear material preferably acrylic. The lens itself is comprised of a half circle curved inward to form an open convex ring or oval. The right and left posterior portion of the device can taper to form tabs 2, before approximating, allowing for expansion and minimizing stress to the device. The tension created by the shape of this device allows for it to self affix.

Figure 3:
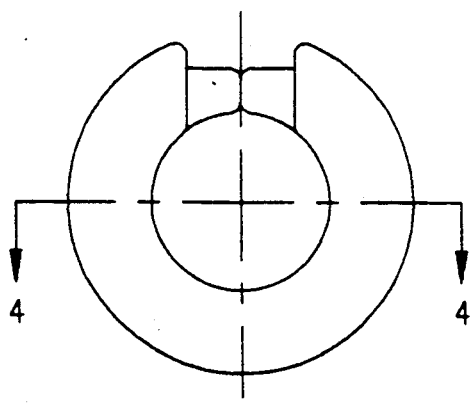
FIG. 3 is a top view.
Figure 4:
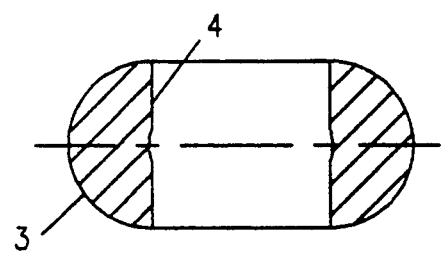
FIG. 4 is a sectional view along lines 4-4 in FIG. 3.

Referring now to FIGS. 3 and 4: FIG. 4 is a sectional view along line 4—4 shown in FIG. 3. FIG. 4 illustrates the symmetrical convexity of the outer surface 3, and the flat top to bottom inner surface 4. The inner surface may have a slight concavity at its horizontal center that can occur as the plastic sucks-in during the cooling process. The inner surface may be constructed with lead-ins to facilitate the invention being slid over labels.

Figure 5:
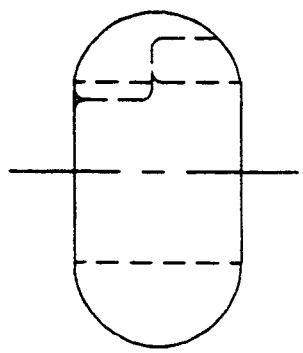
FIG. 5 is a side view.
Figure 6:
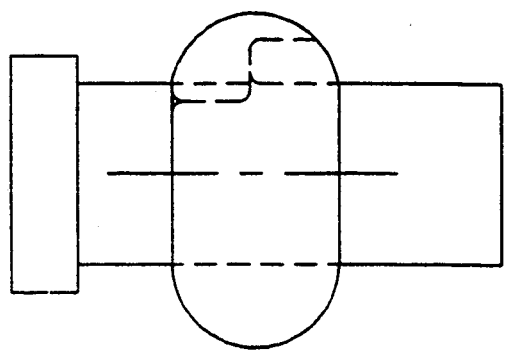
FIG. 6 is a side view shown in combination with a medication vial.

The side view in FIG. 5 illustrates the symmetry of this magnifying device. FIG. 6 illustrates the side view in combination with a round vial.

OPERATION

To use this magnifying device simply slide it onto a vial, bottle, or container. Position it with the convex body 1, over the chosen lines of inscription. Rotate the device so that the opened portion or tabs 2, are over unlabeled areas of the vial. To magnify other lines of text the user simply slides the device up or down the vial or container. This magnifying device stays in place until it is removed to be placed on another vial or other container.

CONCLUSION

Briefly, my curved magnifier comprises: a convex lens curved inward to form a convex circular open ring or oval, and means for self affixing to vials, bottles, containers or other curved objects. This lens can be fabricated economically and effectively from transparent synthetic resins which posses an optimal degree of optical clarity, or glass.

The reader will see that this curved convex magnifier expands the usage of magnification from the two dimensional realm by providing an economical and reliable device that matches the contour of a vial, or other curved object needing magnification. This magnifying device can be used to prevent dangerous and costly medication dispensing errors, and can offer convenience to millions of people every day.

While this magnifying device has been described above, this should not be construed as limiting the scope of the invention, but merely as an illustration of the more crucial embodiment of this invention. Specific materials and shapes were mentioned for the purpose of illustration, and should not be considered limiting. Accordingly, the scope of the invention should be determined not by the embodiment illustrated, but by the appended claims and their legal equivalents.

I claim:
1. An instrument for magnifying lines of text printed on a container, said instrument comprising:
   a lens means for magnifying said lines of text, said lens means having a shape of an open ring, said open ring having a convex outer surface and a flat inner surface curved inward, and having lead-ins notched into said inner surface and
   means for releasably attaching said instrument to said container.
2. The instrument of claim 1 wherein said releasably attaching means includes tabs which are integrally formed at both ends of said open ring.

* * * * *